United States Patent
Hirabara

(10) Patent No.: US 12,239,452 B2
(45) Date of Patent: Mar. 4, 2025

(54) DEVICE FOR CLASSIFYING CONDITION OF SUBJECT AND NON-TRANSITORY COMPUTER-READABLE MEDIUM HAVING RECORDED COMPUTER PROGRAM FOR THE DEVICE

(71) Applicant: NIHON KOHDEN CORPORATION, Tokyo (JP)

(72) Inventor: Hideaki Hirabara, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 399 days.

(21) Appl. No.: 17/783,497

(22) PCT Filed: Dec. 2, 2020

(86) PCT No.: PCT/JP2020/044868
§ 371 (c)(1),
(2) Date: Jun. 8, 2022

(87) PCT Pub. No.: WO2021/117579
PCT Pub. Date: Jun. 17, 2021

(65) Prior Publication Data
US 2023/0068440 A1    Mar. 2, 2023

(30) Foreign Application Priority Data
Dec. 13, 2019   (JP) .................. 2019-225300

(51) Int. Cl.
*A61B 5/00* (2006.01)
*A61B 5/024* (2006.01)

(52) U.S. Cl.
CPC ............ *A61B 5/412* (2013.01); *A61B 5/0053* (2013.01); *A61B 5/024* (2013.01); *A61B 5/7282* (2013.01); *A61B 5/746* (2013.01)

(58) Field of Classification Search
CPC ....... A61B 5/412; A61B 5/0053; A61B 5/024; A61B 5/7282; A61B 5/746; A61B 5/0245; A61B 5/027; G16H 10/60; G16H 50/20

See application file for complete search history.

(56) References Cited

U.S. PATENT DOCUMENTS

| | | |
|---|---|---|
| 2012/0130211 A1 | 5/2012 | Kobayashi et al. |
| 2012/0245439 A1 | 9/2012 | Andre et al. |

(Continued)

FOREIGN PATENT DOCUMENTS

| | | |
|---|---|---|
| JP | 5687994 B2 | 3/2015 |
| JP | 2018-504946 A | 2/2018 |
| JP | 2019-207684 A | 12/2019 |

OTHER PUBLICATIONS

Office Action issued Sep. 12, 2023, issued by the Japan Patent Office in counterpart Japanese Patent Application No. 2019-225300.

(Continued)

*Primary Examiner* — Mark W. Bockelman
(74) *Attorney, Agent, or Firm* — Sughrue Mion, PLLC

(57) ABSTRACT

A condition classifying device includes: an input interface configured to receive first data corresponding to a blood refilling state after ischemia of a subject, and second data corresponding to a physiological parameter that exhibits changes caused by vasodilation of the subject; a processor configured to perform a classification of a condition of the subject related to sepsis based on the first data and the second data; and an output interface configured to output a result of the classification.

14 Claims, 3 Drawing Sheets

(56) References Cited

U.S. PATENT DOCUMENTS

| | | | |
|---|---|---|---|
| 2012/0316892 | A1 | 12/2012 | Huster et al. |
| 2015/0011844 | A1 | 1/2015 | Paradis |
| 2018/0271382 | A1 | 9/2018 | Bezemer et al. |
| 2019/0307405 | A1 | 10/2019 | Terry et al. |
| 2019/0336085 | A1 | 11/2019 | Kayser et al. |
| 2020/0066415 | A1 | 2/2020 | Hettig et al. |

OTHER PUBLICATIONS

Morimura, "Prediction of shock status by quantitative capillary refill time with automatic pressure device for fingertip," Research report of research results of chemical research expenses, Jun. 19, 2018, Total 4 pages.

International Search Report (PCT/ISA/210) dated Feb. 25, 2021 issued by the International Searching Authority in International Application No. PCT/JP2020/044868.

Written Opinion (PCT/ISA/237) dated Feb. 25, 2021issued by the International Searching Authority in International Application No. PCT/JP2020/044868.

Anonymous, "Modified Early Warning Score (MEWS) for Clinical Deterioration", Nov. 15, 2019, 3 pages, https://web.archive.org/web/20191115193738/https://www.mdcalc.com/modified-early-warning-score-mews-clinical-.

Principi, T., et al., "Update in Pediatric Emergency Medicine: Pediatric Resuscitation, Pediatric Sepsis, Interfacility Transport of the Pediatric Patient, Pain and sedation in the Emergency Department, Pediatric Trauma", Apr. 17, 2018, Springer International Publishing, Cham, pp. 223-249.

Anonymous, "Capillary Refill", Wikipedia, Nov. 13, 2013, https://en.wikipedia.org/w/index.php?title=Capillary_refill&oldid=878269648, 2 pages.

Shinozaki, K., et al., "Blood refill time: Clinical bedside monitoring of peripheral blood perfusion using pulse oximetry sensor and mechanical compression", American Journal of Emergency Medicine, vol. 36, No. 12, Apr. 5, 2018, pp. 2310-2312 (3 pages).

[Fig. 1]
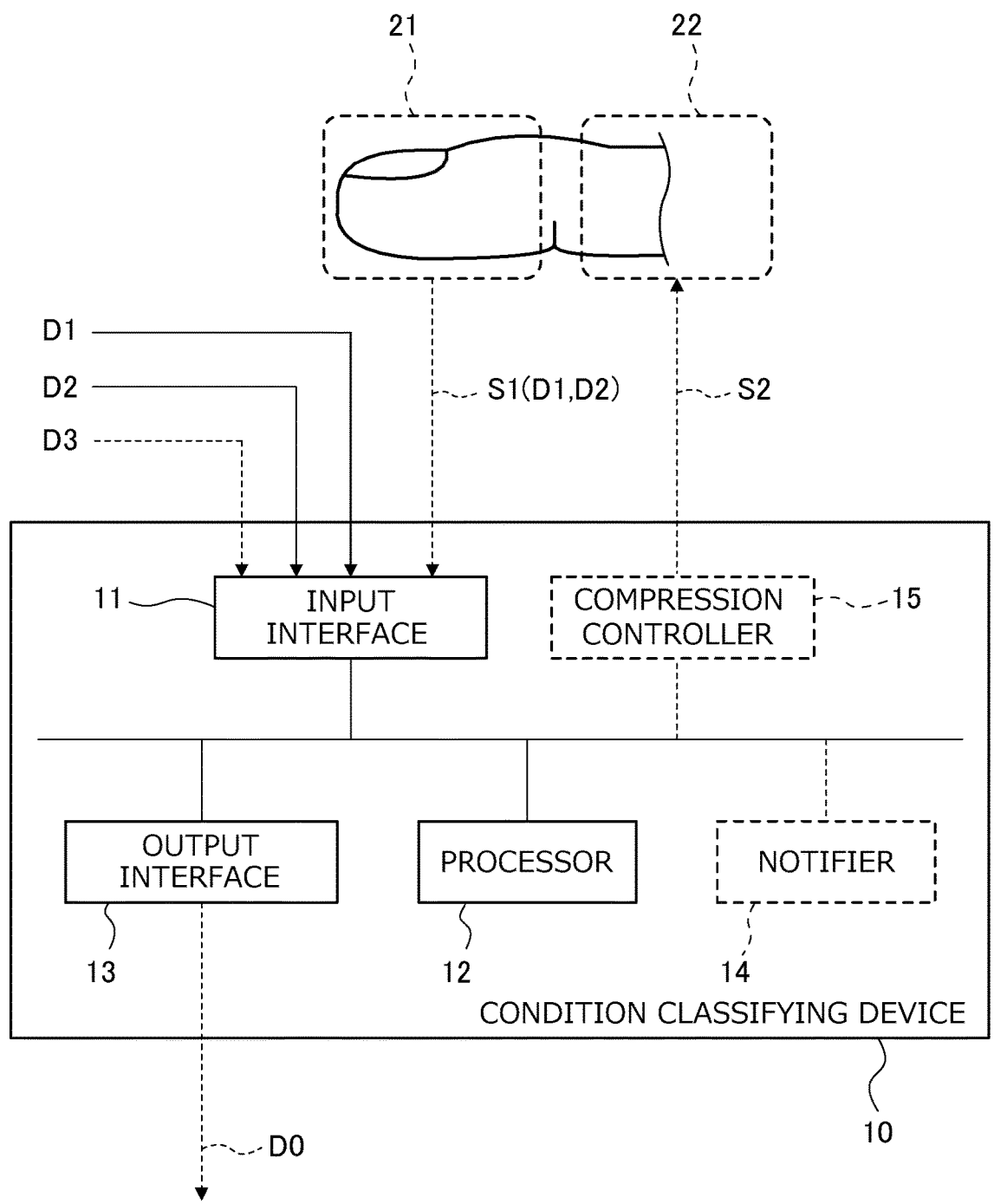

[Fig. 2]
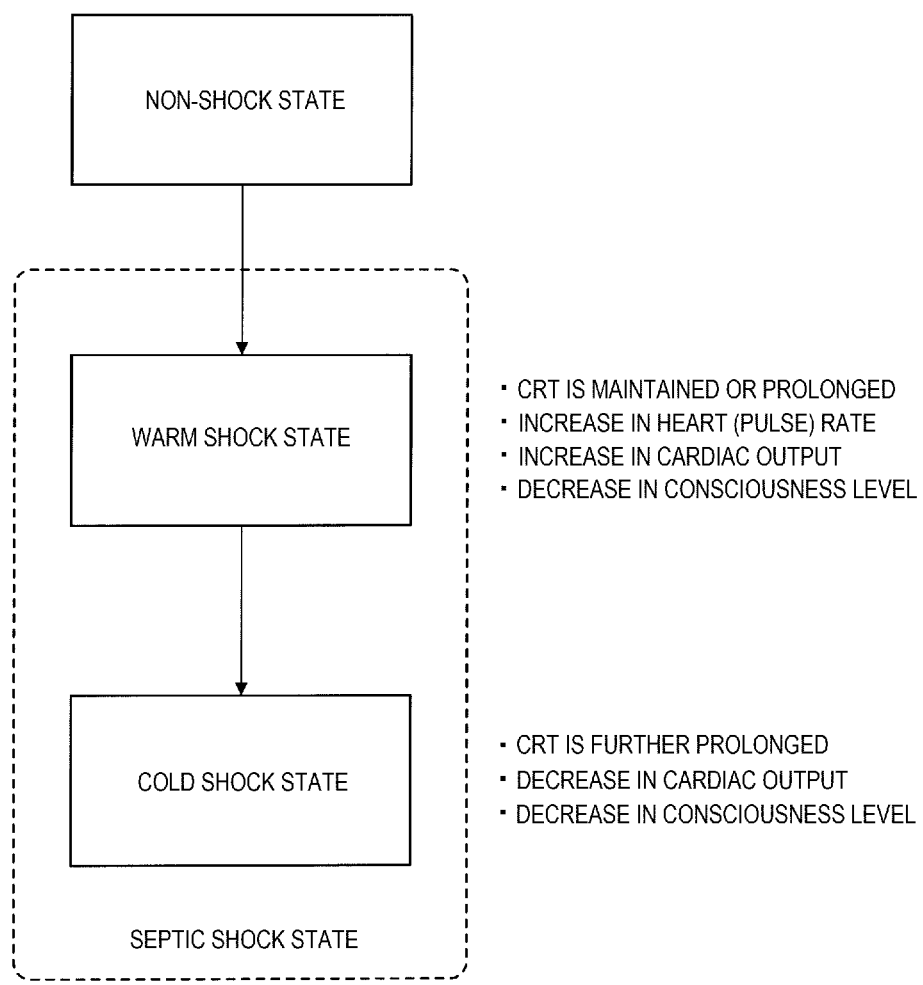

[Fig. 3]
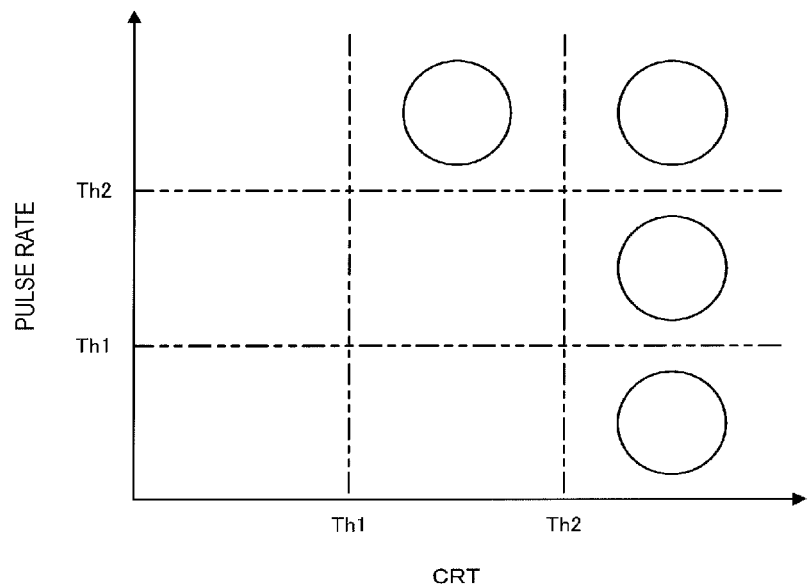
[Fig. 4]
|  | < Th1 | ≥ Th1, < Th2 | ≥ Th2 |
|---|---|---|---|
| CRT | 0 | 2 | 4 |
| PULSE RATE | 0 | 0 | 2 |

DEVICE FOR CLASSIFYING CONDITION OF SUBJECT AND NON-TRANSITORY COMPUTER-READABLE MEDIUM HAVING RECORDED COMPUTER PROGRAM FOR THE DEVICE

TECHNICAL FIELD

The presently disclosed subject matter relates to a device for classifying a condition of a subject, and a non-transitory computer-readable medium having recorded a computer program adapted to be executed by a processor included in the device.

BACKGROUND

Japanese Patent No. 5687994 discloses a device for quantitatively measuring a capillary refill time (CRT) of a subject using the principle of pulse oximetry. The CRT is one of indices that can indicate a condition of a subject related to sepsis.

SUMMARY

Technical Problem

It is demanded to enhance the classification ability of a condition of a subject related to the sepsis.

Solution to Problem

A first illustrative aspect of the presently disclosed subject matter provides a condition classifying device comprising:
an input interface configured to receive first data corresponding to a blood refilling state after ischemia of a subject, and second data corresponding to a physiological parameter that exhibits changes caused by vasodilation of the subject;
a processor configured to perform a classification of a condition of the subject related to sepsis based on the first data and the second data; and
an output interface configured to output a result of the classification.

A second illustrative aspect of the presently disclosed subject matter provides a non-transitory computer-readable medium having recorded a computer program adapted to be executed by a processor of a condition classifying device, the computer program being configured to, when executed, cause the condition classifying device to:
receive first data corresponding to a blood refilling state after ischemia of a subject, and second data corresponding to a physiological parameter that exhibits changes caused by vasodilation of the subject;
perform a classification of a condition of the subject related to sepsis based on the first data and the second data; and
output a result of the classification.

At the time when the condition of the subject has just transited to a warm shock state that appears in the early stage of the sepsis, the state of blood refilling after ischemia exhibits no remarkable difference from a non-shock state, but exhibits gradual changes along with the progress of the warm shock state. Accordingly, it is difficult to distinguish the warm shock state from the non-shock state if attention is paid only to the blood refilling state after the ischemia.

On the other hand, changes in a certain physiological parameter caused by vasodilation may exhibit a relatively remarkable difference from the non-shock state even in the early stage of the septic shock state. In other words, it is possible to classify the septic shock state including the warm shock state at an earlier stage by referring to both of the blood refilling state after the ischemia and the changes in the physiological parameter caused by the vasodilation that are based on different mechanisms. Accordingly, it is possible to enhance the classification ability of a condition of a subject related to the sepsis.

A third illustrative aspect of the presently disclosed subject matter provides a condition classifying device comprising:
an input interface configured to receive first data corresponding to a blood refilling state after ischemia of a subject, and second data corresponding to a level of consciousness of the subject;
a processor configured to perform a classification of a condition of the subject related to sepsis based on the first data and the second data; and
an output interface configured to output a result of the classification.

A fourth illustrative aspect of the presently disclosed subject matter provides a non-transitory computer-readable medium having recorded a computer program adapted to be executed by a processor of a condition classifying device, the computer program being configured to, when executed, cause the condition classifying device to:
receive first data corresponding to a blood refilling state after ischemia of a subject, and second data corresponding to a level of consciousness of the subject;
perform a classification of a condition of the subject related to sepsis based on the first data and the second data; and
output a result of the classification.

At the time when the condition of the subject has just transited to a warm shock state that appears in the early stage of the sepsis, the state of blood refilling after ischemia exhibits no remarkable difference from a non-shock state, but exhibits gradual changes along with the progress of the warm shock state. Accordingly, it is difficult to distinguish the warm shock state from the non-shock state if attention is paid only to the blood refilling state after the ischemia.

On the other hand, changes in a level of consciousness exhibit a relatively remarkable difference from the non-shock state even in the early stage of the septic shock state. In other words, it is possible to classify the septic shock state including the warm shock state at an earlier stage by referring to both of the blood refilling state after the ischemia and the changes in the level of consciousness that are based on different mechanisms. Accordingly, it is possible to enhance the classification ability of a condition of a subject related to the sepsis.

BRIEF DESCRIPTION OF DRAWINGS

FIG. 1 illustrates a functional configuration of a condition classifying device according to one embodiment.

FIG. 2 illustrates progression of a septic shock state.

FIG. 3 illustrates one example of processing performed by the condition classifying device of FIG. 1.

FIG. 4 illustrates another example of processing performed by the condition classifying device of FIG. 1.

DESCRIPTION OF EMBODIMENTS

Examples of embodiments will be described below in detail with reference to the accompanying drawings.

FIG. 1 illustrates a functional configuration of a condition classifying device 10 according to an embodiment. The condition classifying device 10 is a device for classifying a condition of a subject related to the sepsis.

The condition classifying device 10 includes an input interface 11. The input interface 11 is configured to receive first data D1. The first data D1 corresponds to a capillary refill time (CRT) of the subject.

The CRT is acquired as a time period from a time when a living tissue such as a finger tip of the subject is compressed to form an ischemic state to a time when the living tissue gains color after the compression is released. That is, the CRT may be an index that represents the blood refilling state of the subject after the ischemia. The CRT may be obtained visually or by quantitative measurement using the principle of pulse oximetry. Since these are well-known techniques, detailed descriptions thereof will be omitted.

In a case where the CRT is acquired visually, the first data D1 may be a numerical value inputted by the user. The numerical value may be inputted through a user interface provided in the condition classifying device 10, or may be inputted from an external device independent of the condition classifying device 10 by way of wired communication or wireless communication. The numerical value may be inputted by manual operation of the user interface or through voice input.

When the CRT is acquired using the principle of pulse oximetry, a probe is attached to the living tissue of the subject. The probe includes a light emitting element and a light detecting element. The light emitting element emits light toward the living tissue. The light that has passed through or reflected by the living tissue is incident on the light detecting element. The light detecting element outputs a signal corresponding to the intensity of the incident light. In this case, the first data D1 may be a signal outputted from the light detecting element.

The input interface 11 is configured to receive second data D2. The second data D2 corresponds to a pulse rate of the subject. The pulse rate is an example of a physiological parameter that exhibit changes caused by vasodilation of the subject.

The condition classifying device 10 includes a processor 12. The processor 12 is configured to classify a condition of the subject related to the sepsis based on the first data D1 and the second data D2.

A patient who develops the sepsis may fall into a severe condition called a septic shock state. Specifically, the patient falls into a condition called the warm shock state in an early stage, and subsequently transits a condition called a cold shock state. The warm shock state causes a strong vasodilation so that a peripheral vascular resistance is reduced. As a result, a heart rate and a cardiac output increase as well as extremities get warmer. The cold shock state causes a vasoconstriction. Accordingly, the cardiac output decreases and the extremities get cooler, resulting in circulatory failure. In other words, an onset of the sepsis can be estimated if is found that the condition of the subject corresponds to the warn shock state or the cold shock state.

FIG. 2 illustrates progression of the sepsis from the non-shock state to the cold shock state by way of the warm shock state, along with trends of various physiological parameters that may be identified in each state.

In the warm shock state, the CRT tends to be maintained or prolonged as compared to the non-shock state. On the other hand, the pulse rate tends to increase in order to maintain the circulation.

In the cold shock state, the CRT tends to be further prolonged compared to the non-shock state due to the decreased cardiac output and the circulatory failure.

For example, as illustrated in FIG. 3, two threshold values Th1 and Th2 may be set for each of the CRT and the pulse rate. The processor 12 is configured to determine whether the subject is in the septic shock state by comparing the value of the CRT corresponding to the first data D1 and the value of the pulse rate corresponding to the second data D2 with these thresholds. In FIG. 3, a circle represents that it is classified that the patient is in the septic shock state.

Alternatively, as illustrated in FIG. 4, a score may be set for each threshold range. In this case, an evaluation score can be calculated by adding or multiplying the score corresponding to each value of the CRT and the pulse rate. When the evaluation score exceeds a prescribed threshold value, it is classified that the subject is in the septic shock state. In this case, a weight may be assigned to either the CRT or the pulse rate. In the example illustrated in FIG. 4, the value of the CRT is set so as to have a greater influence on the classification.

As described above, since a subject in the warm shock state may be caused to exhibit a strong vasodilation, a value of the CRT at the time when the subject has just transited to the warm shock state exhibits no remarkable difference from a value of the CRT at the time when the subject is in the non-shock state, but the value of the CRT may be prolonged along with the progress of the warm shock state. Accordingly, in a case where attention is paid only to the value of the CRT, it is difficult to distinguish the warm shock state from the non-shock state in connection with the threshold value Th1, as well as to distinguish the cold shock state from the warm shock state in connection with the threshold value Th2. That is, it is difficult to distinguish the non-shock state from the warm shock state.

On the other hand, changes in the pulse rate exhibit a relatively remarkable difference from the non-shock state even in the early stage of the septic shock state. In other words, it is possible to classify the septic shock state including the warm shock state at an earlier stage by referring to both of the CRT and the pulse rate that are based on different mechanisms. Accordingly, it is possible to enhance the classification ability of a condition of a subject related to the sepsis.

As illustrated in FIG. 1, the condition classifying device 10 includes an output interface 13. The output interface 13 is configured to output a result of the classification performed by the processor 12.

As an example, the output interface 13 may be a user interface provided in the condition classifying device 10. In this case, the result of the classification is notified to the user through at least one of a visual notification, an audible notification, and a haptic notification.

As another example, the output interface 13 may be a communication interface that transmits the data DO corresponding to the result of the classification to a device independent of the condition classifying device 10. The data DO may be transmitted by wired communication or wireless communication.

As illustrated in FIG. 2, the pulse rate is a physiological parameter that has different tendencies to change from the CRT for the warm shock state and the cold shock state. Specifically, the CRT tends to have a higher value in the cold shock state than in the warm shock state. On the other hand, the pulse rate tends to have a higher value in the warm shock state.

By configuring the second data D2 so as to correspond to such a physiological parameter, the processor 12 can determine whether the subject is in the warm shock state or the cold shock state by referring to both the first data D1 and the second data D2. For example, if the CRT has a relatively low value and the pulse rate has a relatively high value, it can be classified that the subject is in the warm shock state. Conversely, if the CRT has a relatively high value, it can be classified that the subject is in the cold shock state. Accordingly, it is possible to provide a more detailed result of the classification as to the condition of the subject related to the sepsis. In particular, since the warm shock state can be classified, it is possible to prompt a medical worker to take care of the subject prior to the transition to the cold shock state that is a more severe condition.

Both the CRT and the pulse rate are physiological parameters that can be non-invasively obtained from a subject.

By selecting the physiological parameter corresponding to the first data D1 and the physiological parameter corresponding to the second data D2 in this manner, it is possible to classify a condition of a subject related to the sepsis without invasion. Accordingly, it is possible to suppress an increase in the burden on the subject.

Both the CRT and the pulse rate are physiological parameters that can be obtained using the principle of pulse oximetry.

Accordingly, as illustrated in FIG. 1, it is possible to obtain the first data D1 and the second data D2 from a common signal S1 outputted from a pulse oximetry probe 21 attached to the subject. As a result, since it is possible to suppress an increase in the number of measurement instruments attached to the subject, it is possible to suppress an increase in the burden on both the subject and the medical worker.

As illustrated in FIG. 1, the condition classifying device 10 may include a notifier 14. The notifier 14 may be configured to notify, in a case where a compression of a living tissue for acquiring the CRT is performed by a manual operation of a user, at least one of a timing at which the compression is started and a timing at which the compression is released. The notification to the user may be performed through at least one of a visual notification, an audible notification, and a haptic notification. The operation of the notifier 14 may be controlled by the processor 12.

According to such a configuration, since it is possible to suppress variations in the compressing condition of the living tissue for each manual operation, it is possible to suppress degradation in the accuracy of the classification performed by the condition classifying device 10.

Alternatively, as illustrated in FIG. 1, the condition classifying device 10 may include a compression controller 15. The compression controller 15 is configured to output a control signal S2 for controlling the operation of a compression device 22 configured to compress the living tissue of the subject. The compression device 22 may be implemented by an actuator or the like. The operation of the compression controller 15 may be controlled by the processor 12.

The compression device 22 may be configured to include an air bladder adapted to be attached to a living tissue of a subject, and a pump for increasing or decreasing air pressure in the air bladder. In this case, the control signal S2 is configured to control the operation of the pump. The pump may be provided in the condition classifying device 10.

According to such a configuration, it is possible to automate the process from the generation of the ischemic state to the classification of the condition related to the sepsis. For example, by operating the compression device 22 every elapse of a prescribed time period, it is possible to realize continuous automatic condition monitoring of the subject.

As illustrated in FIG. 1, the input interface 11 may be configured to receive third data D3. The third data D3 corresponds to the level of consciousness of the subject. The level of consciousness is defined by numerical values defined by JCS (Japan Coma Scale) or GCS (Glasgow Coma Scale), for example. The numerical value can be inputted by a user as the third data D3. The numerical value may be inputted through a user interface provided in the condition classifying device 10, or may be inputted from an external device independent of the condition classifying device 10 by way of wired communication or wireless communication. The numerical value may be inputted by manual operation of the user interface or through voice input.

As illustrated in FIG. 2, in the septic shock state, the level of consciousness of the subject tends to decrease as compared with the non-shock state. The processor 12 is configured to classify a condition of a subject related to the sepsis based on the first data D1, the second data D2, and the third data D3.

By additionally referring to the level of consciousness, the classifying condition can be defined in more detail. Accordingly, it is possible to further enhance the classification ability of a condition of a subject related to the sepsis.

It should be noted that the condition classifying device 10 may be configured so as to cause the second data D2 to correspond to the level of consciousness instead of the physiological parameter that exhibit changes caused by the vasodilation of the subject. The CRT and the level of consciousness are physiological parameters that have different tendencies to change for the non-shock state and the septic shock state. Specifically, the CRT tends to have a higher value in the septic shock state than in the non-shock state. On the other hand, the level of consciousness tends to have a lower value in the septic shock state than in the non-shock state.

As described above, it is difficult to distinguish the warm shock state from the non-shock state if attention is paid only to the value of the CRT. On the other hand, changes in a level of consciousness exhibit a relatively remarkable difference from the non-shock state even in the early stage of the septic shock state. In other words, it is possible to classify the septic shock state including the warm shock state at an earlier stage by referring to both of the CRT and the level of consciousness that are based on different mechanisms. For example, if the CRT has a relatively low value and the level of consciousness has a relatively high value, it can be classified that the subject is in the warm shock state. Conversely, if the CRT has a relatively high value and the level of consciousness has a relatively low value, it can be classified that the subject is in the septic shock state. Accordingly, it is possible to enhance the classification ability of a condition of a subject related to the sepsis.

The processor 12 having the above-described functions may be implemented by one or more general-purpose microprocessors configured to cooperate with one or more general-purpose memories. Examples of the general-purpose microprocessor include a CPU and an MPU. Examples of the general-purpose memory include a RAM and a ROM. In this case, a computer program for executing the above-described processing may be stored in the ROM. The ROM is an example of a non-transitory computer-readable medium having stored a computer program. The processor designates at least a part of the program stored in the ROM, loads the program on the RAM, and executes the processing described above in cooperation with the RAM. The above-mentioned computer program may be pre-installed in a general-purpose memory, or may be downloaded from an external server via a communication network and installed in the general-purpose memory. In this case, the external server is an example of a non-transitory computer-readable medium having stored a computer program.

The processor 12 may be implemented by one or more dedicated integrated circuits capable of executing the computer program described above. Examples of the dedicated integrated circuit include a microcontroller, an ASIC, and an FPGA. In this case, the above-mentioned computer program is pre-installed in the storage element included in the dedicated integrated circuit. The storage element is an example of a storage medium having stored a computer program. The processor 12 may also be implemented by a combination of the general-purpose microprocessor and the dedicated integrated circuit.

The above embodiments are mere examples for facilitating understanding of the presently disclosed subject matter. The configuration according to each of the above embodiments can be appropriately modified without departing from the gist of the presently disclosed subject matter.

The first data D1 need not necessarily correspond to the CRT as long as it reflects the blood refilling state after the ischemia of the subject. For example, in a case where the first data D1 is acquired through the pulse oximetry probe, the first data D1 may correspond to a change amount of the light-detecting intensity in the light detecting element until a prescribed time period elapses after the compression of the living tissue is released.

As long as the physiological parameter that exhibit changes caused by the vasodilation of the subject, the second data D2 does not necessarily have to correspond to the pulse rate. The second data D2 may correspond to a heart rate, a cardiac output, a cardiac index, a stroke volume, a stroke volume change rate, a systemic vascular resistance, a systemic vascular resistance index, a central venous oxygen saturation, and the like.

In the warm shock state, since a strong vasodilation is caused to exhibit, the systemic vascular resistance and the systemic vascular resistance index are decreased. In the cold shock state, since a dilatation capability of the peripheral vessel is reduced, the systemic vascular resistance and the systemic vascular resistance index are increased. That is, each of the systemic vascular resistance and the systemic vascular resistance index is an example of a physiological parameter that has different tendencies to change from the CRT for the warm shock state and the cold shock state.

The heart rate, the cardiac output, the cardiac index, the stroke volume, the stroke volume change rate, and a central venous oxygen saturation exhibit the same trend as the pulse rate with the progression of the sepsis. That is, each of the heart rate, the cardiac output, the cardiac index, the stroke volume, the stroke volume change rate, and the central venous oxygen saturation is an example of a physiological parameter that has different tendencies to change from the CRT for the warm shock state and the cold shock state.

The heart rate is a physiological parameter that may be non-invasively obtained from a subject. The heart rate may be acquired through an electrocardiogram sensor or the like attached to the subject. The cardiac output, the cardiac index, the stroke volume, the stroke volume change rate, the systemic vascular resistance, the systemic vascular resistance index, and the central venous oxygen saturation can be invasively obtained using a catheter.

The present application is based on Japanese Patent Application No. 2019-225300 filed on Dec. 13, 2019, the entire contents of which are hereby incorporated by reference.

The invention claimed is:

1. A condition classifying device comprising:
an input interface configured to receive first data corresponding to a blood refilling state after ischemia of a subject, and second data corresponding to a physiological parameter that exhibits changes caused by vasodilation of the subject;
a processor configured to perform a classification of a condition of the subject related to sepsis based on the first data and the second data;
a compression controller configured to drive an actuator to cause an ischemic state in the subject;
an output interface configured to output a result of the classification,
wherein the condition of the subject includes one of a warm shock state and a cold shock state,
wherein the input interface comprises a pulse oximetry probe, and
wherein the processor is configured to:
drive the actuator to cause ischemia in the subject,
in a blood refilling state after the ischemia, receive the first data and the second data through the pulse oximetry probe,
detect a change in the first data and a change in the second data after the ischemia,
based on the change of the first data and the change of the second data after the ischemia, perform classification of the subject into the warm shock state and the cold shock state.

2. The condition classifying device according to claim 1, wherein the second data corresponds to a physiological parameter that has different tendencies to change from the blood refilling state after ischemia for the warm shock state and the cold shock state.

3. The condition classifying device according to claim 1, wherein the second data corresponds to a physiological parameter that can be non-invasively obtained from the subject.

4. The condition classifying device according to claim 3, wherein the second data corresponds to a pulse rate.

5. The condition classifying device according to claim 1, wherein the first data corresponds to a capillary refill time of the subject.

6. The condition classifying device according to claim 1, further comprising:
a notifier configured to notify at least one of a timing when compression of a living tissue of the subject is started to obtain the first data, and a timing when the compression is released.

7. The condition classifying device according to claim 1, wherein the input interface is configured to receive third data corresponding to a level of consciousness of the subject; and
wherein the processor is configured to perform classifying the condition of the subject related to sepsis based on the first data, the second data, and the third data.

8. The condition classifying device according to claim 1, wherein the processor is configured to perform a classification of a condition of the subject related to sepsis based only on the first data and the second data.

9. The condition classifying device according to claim 1, wherein the first data corresponds to a capillary refill time of the subject, and the second data corresponds to a pulse rate, and wherein the first data and the second data are obtained from a common signal outputted from the pulse oximetry probe.

10. The condition classifying device according to claim 1, wherein the first data corresponds to a capillary refill time, and the second data corresponds to a pulse rate wherein the processor is further configured to:
in a state in which the change of the first data decreases and the change of the second data increases, classify the subject into the warm shock state, and
in a state in which the change of the first data increases and the change of the second data increases or decreases, classify the subject into the cold shock state.

11. A condition classifying device comprising:
an input interface configured to receive first data corresponding to a blood refilling state after ischemia of a subject, second data corresponding to a physiological parameter that exhibits changes caused by vasodilation of the subject, and third data corresponding to a level of consciousness of the subject;
a processor configured to perform a classification of a condition of the subject related to sepsis based on the first data, the second data, and the third data;
a compression controller configured to drive an actuator to cause an ischemic state in the subject; and
an output interface configured to output a result of the classification,
wherein the condition of the subject includes one of a warm shock state and a cold shock state
wherein the processor is configured to:
drive the actuator to cause ischemia in the subject,
in a blood refilling state after the ischemia, receive the first data and the second data through the pulse oximetry probe,
receive third data corresponding to a level of consciousness of the subject through the input interface,
detect a change in the first data, a change in the second data, and a change in the third data after the ischemia,
based on the change of the first data, the change of the second data, and the change of the third data after the ischemia, perform classification of the subject into the warm shock state and the cold shock state.

12. The condition classifying device according to claim 11, wherein the first data corresponds to a capillary refill time, the second data corresponds to a pulse rate, and the third data corresponds to a value defined by one of Japan Coma Scale and Glasgow Coma Scale,
wherein the processor is further configured to:
in a state in which the change of the first data decreases, and the change of the second data increases or the change of the third data increases, classify the subject into the warm shock state,
in a state in which the change of the first data increases and the change of the second data increases or decreases, classify the subject into the cold shock state, and
in a state in which the first data increases and the third data decreases, classify the subject into a septic shock state.

13. A non-transitory computer-readable medium having recorded a computer program adapted to be executed by a processor of a condition classifying device, the computer program being configured to, when executed, cause the condition classifying device to:
receive first data corresponding to a blood refilling state after ischemia of a subject, second data corresponding to a physiological parameter that exhibits changes caused by vasodilation of the subject, and third data corresponding to a level of consciousness of the subject,
wherein the receiving the first data, the second data, and the third data comprises:
driving an actuator of a compression controller to cause ischemia in the subject,
in a blood refilling state after the ischemia, controlling a pulse oximetry probe to receive the first data and the second data through the pulse oximetry probe, and
receiving third data through an input interface;
perform a classification of a condition of the subject related to sepsis based on the first data, the second data, and the third data,
wherein the condition of the subject includes one of a warm shock state and a cold shock state,
wherein the performing the classification of the condition comprises:
detecting a change in the first data, a change in the second data, and a change in the third data after the ischemia,
based on the change of the first data, the change of the second data, and the change of the third data after the ischemia, performing classification of the subject into the warm shock state and the cold shock state; and
output a result of the classification.

14. The non-transitory computer-readable medium of claim 13, wherein the performing the classification of the subject comprises:
in a state in which the change of the first data decreases, and the change of the second data increases or the change of the third data increases, classifying the subject into the warm shock state,
in a state in which the change of the first data increases and the change of the second data increases or decreases, classifying the subject into the cold shock state, and
in a state in which the first data increases and the third data decreases, classifying the subject into a septic shock state.

* * * * *